(12) United States Patent
Mundie et al.

(10) Patent No.: US 7,406,453 B2
(45) Date of Patent: Jul. 29, 2008

(54) LARGE-SCALE INFORMATION COLLECTION AND MINING

(75) Inventors: Craig J. Mundie, Redmond, WA (US); David E. Heckerman, Bellevue, WA (US); Nebojsa Jojic, Redmond, WA (US); Randy J. Hinrichs, Sammamish, WA (US)

(73) Assignee: Microsoft Corporation, Redmond, WA (US)

( * ) Notice: Subject to any disclaimer, the term of this patent is extended or adjusted under 35 U.S.C. 154(b) by 97 days.

(21) Appl. No.: 11/266,974

(22) Filed: Nov. 4, 2005

(65) Prior Publication Data

US 2007/0106626 A1 May 10, 2007

(51) Int. Cl.
*G06E 1/00* (2006.01)
*G06E 3/00* (2006.01)
*G06F 15/18* (2006.01)
*G06G 7/00* (2006.01)

(52) U.S. Cl. ...................................................... 706/20
(58) Field of Classification Search .................... 706/20
See application file for complete search history.

(56) References Cited

U.S. PATENT DOCUMENTS

| | | | | | |
|---|---|---|---|---|---|
| 5,544,044 | A | * | 8/1996 | Leatherman ................... 705/3 |
| 5,562,596 | A | * | 10/1996 | Pincus et al. .................. 600/17 |
| 5,572,421 | A | * | 11/1996 | Altman et al. .................. 705/3 |
| 5,659,741 | A | * | 8/1997 | Eberhardt ................. 707/104.1 |
| 6,157,921 | A | * | 12/2000 | Barnhill ....................... 706/16 |
| 6,287,254 | B1 | * | 9/2001 | Dodds ........................ 600/300 |
| 6,292,771 | B1 | * | 9/2001 | Haug et al. ..................... 704/9 |
| 6,311,163 | B1 | | 10/2001 | Sheehan et al. |
| 6,317,700 | B1 | * | 11/2001 | Bagne ........................ 702/181 |
| 6,424,996 | B1 | * | 7/2002 | Killcommons et al. ...... 709/206 |
| 6,516,288 | B2 | * | 2/2003 | Bagne ........................ 702/179 |
| 6,537,213 | B2 | * | 3/2003 | Dodds ........................ 600/300 |
| 6,564,207 | B1 | | 5/2003 | Abdoh |
| 6,639,515 | B2 | * | 10/2003 | Hougaard ................ 340/573.1 |

(Continued)

OTHER PUBLICATIONS

Infrastructure for Web-GIS based interoperable SARS information system Xiaolin Lu; Computer Supported Cooperative Work in Design, 2004. Proceedings. The 8th International Conference on vol. 1, May 26-28, 2004 pp. 234-239 vol. 1.*

(Continued)

*Primary Examiner*—Michael B Holmes
(74) *Attorney, Agent, or Firm*—Amin, Turocy & Calvin, LLP

(57) ABSTRACT

The methods/systems described herein facilitate large-scale data collection and aggregation. One exemplary system that facilitates large-scale reporting of health-related data comprises a data collection component, a database and an aggregation component. The data collection component can collect health-related data on a large-scale from a non-selected population. The database can store at least some of the health-related data. The aggregation component can facilitate automatically ascertaining at least one pattern from the health-related data at least in part by applying one or more statistical, data-mining or machine-learning techniques to the database. One exemplary method of extracting health observations from information obtained on a macro-scale comprises receiving information about a plurality of self-selected subjects, pooling the information, mining the pooled information at least in part by employing a data-mining algorithm to infer one or more health observations from the pooled information, and monetizing the one or more health observations.

20 Claims, 11 Drawing Sheets

U.S. PATENT DOCUMENTS

| | | | |
|---|---|---|---|
| 6,669,631 | B2 | 12/2003 | Norris et al. |
| 6,730,023 | B1* | 5/2004 | Dodds .................... 600/300 |
| 6,778,809 | B2* | 8/2004 | Morimoto ................ 455/11.1 |
| 6,789,091 | B2 | 9/2004 | Gogolak |
| 6,820,070 | B2 | 11/2004 | Goldman et al. |
| 6,920,448 | B2 | 7/2005 | Kincaid et al. |
| 6,945,458 | B1 | 9/2005 | Shah et al. |
| 6,947,933 | B2 | 9/2005 | Smolsky |
| 6,980,962 | B1* | 12/2005 | Arganbright et al. ......... 705/26 |
| 6,980,999 | B1* | 12/2005 | Grana .................... 707/104.1 |
| 7,024,370 | B2* | 4/2006 | Epler et al. .................. 705/3 |
| 7,029,441 | B2* | 4/2006 | Dodds .................... 600/300 |
| 7,134,995 | B2* | 11/2006 | Dodds .................... 600/300 |
| 7,359,871 | B1* | 4/2008 | Paasche et al. ............. 705/26 |
| 2002/0022973 | A1* | 2/2002 | Sun et al. ..................... 705/3 |
| 2002/0026103 | A1* | 2/2002 | Norris et al. ............. 600/300 |
| 2002/0039990 | A1* | 4/2002 | Stanton, Jr. .................. 514/1 |
| 2003/0093301 | A1* | 5/2003 | Chesney et al. .............. 705/3 |
| 2003/0225597 | A1 | 12/2003 | Levine |
| 2004/0064731 | A1* | 4/2004 | Nguyen et al. ............. 709/224 |
| 2005/0066201 | A1* | 3/2005 | Goodman et al. .......... 713/202 |
| 2005/0234740 | A1 | 10/2005 | Krishnan et al. |

OTHER PUBLICATIONS

Automated reading and mining of pre-hospital care reports Govindaraju, V.; Milewski, R.; Computer-Based Medical Systems, 2001. CBMS 2001. Proceedings. 14th IEEE Symposium on Jul. 26-27, 2001 pp. 152-157 Digital Object Identifier 10.1109/CBMS.2001.941713.*

An OLAP-Enabled Software Environment for Modeling Patient Flow Vasilakis, C.; El-Darzi, E.; Choutas, P.; Intelligent Systems, 2006 3rd International IEEE Conference on Sep. 2006 pp. 261-266 Digital Object Identifier 10.1109/IS.2006.348428.*

Automated Healthcare Data Mining Based on a Personal Dynamic Healthcare System Takeuchi, H.; Kodama, N.; Hashiguchi, T.; Hayashi, D.; Engineering in Medicine and Biology Society, 2006. EMBS '06. 28th Annual International Conference of the IEEE Aug. 2006 pp. 3604-3607 Digital Object Identifier 10.1109/IEMBS.2006.259228.*

Predicting Breast Tumor via Mining DNA Viruses with Decision Tree Mu-Chen; Hung-Chang Liao; Cheng-Lung Huang; Systems, Man and Cybernetics, 2006. SMC '06. IEEE International Conference on vol. 5, Oct. 8-11, 2006 pp. 3585-3589 Digital Object Identifier 10.1109/ICSMC.2006.384685.*

Usage of OLAP-means of the system "analytics" for the problem of health protection Dudina, Y.V.; Ishenin, P.R.; Modern Techniques and Technologies, 2003. MTT 2003. Proceedings of the 9th International Scientific and Practical Conference of Students, Post-graduates and Young Scientists Apr. 7-11, 2003 pp. 150-152.*

Correlation analysis for decision support with applications to law enforcement Brown, D.E.; Hagen, S.C.; Systems, Man, and Cybernetics, 1999. IEEE SMC '99 Conference Proceedings. 1999 IEEE International Conference on vol. 6, Oct. 12-15, 1999 pp. 1074-1078 vol. 6 Digital Object Identifier 10.1109/ICSMC.1999.816733.*

\* cited by examiner

Enter Answer Here

FIG. 6

LARGE-SCALE INFORMATION COLLECTION AND MINING

BACKGROUND

Many industries benefit from information technologies (IT) that facilitate collecting and drawing conclusions from aggregated data. Generally, the larger the data set, the better the conclusions that can be drawn from the data. However, such a task is complex, time-consuming and costly to perform on a large-scale.

Moreover, some industries face unique IT obstacles that further increase the difficulties of large-scale data acquisition and management. For instance, because health histories generally are stored in private, non-uniform databases, assembling this data on a large-scale would be extremely expensive. By way of another example, collecting and aggregating drug safety information is an important but challenging IT task. To address the potential for harmful drug effects, many countries establish government agencies to approve a pharmaceutical or medical device product before it can be sold to the public. These agencies usually require proof of efficacy and of an acceptable safety profile before the pharmaceuticals and medical devices are approved for sale. Typically the proof is obtained by conducting clinical trials on selected populations. These trials usually take many months and are quite expensive to conduct. In addition, some countries have post-market surveillance mechanisms in place, such as mandatory and voluntary adverse event reporting. However, delays inherent in the current systems have resulted in medications and devices with unacceptable risks remaining on the market during the time the data is being collected and aggregated.

SUMMARY

This summary is not an extensive overview of the invention. It is not intended to identify key/critical elements of the invention or to delineate the scope of the invention. The sole purpose of this summary is to present some concepts relating to the invention in a simplified form as a prelude to the more detailed description that follows.

The methods and systems described herein facilitate collecting and mining very large amounts of data. The data can be of any type including but not limited to health-related information, and thus, the methods and systems are not limited to healthcare applications. Healthcare industry applications of the methods and systems described herein include identifying unknown/unintended drug reactions (e.g., surrogate Phase IV clinical trials), drug-drug interactions and off-label drug interactions. In one embodiment, health-related information can be obtained from a wide variety of sources including but not limited to directly from patients via a computerized service, such as a web site using a web form for entering information. The data can be correlated with information from a variety of different sources and/or systems to facilitate drawing conclusions relating to the patient's health. Any source having pertinent information can subscribe to the web service to provide information. Other sources of information include insurers, providers (e.g., doctors, nurses, hospitals, nursing homes, etc.) and devices (e.g., pacemakers, smart scale, etc.).

The data can be provided explicitly or automatically culled from existing information (e.g., frequency of prescription refills as an indication of whether a patient is taking their medication as prescribed). Although the data so obtained may be noisy, machine-learning/data-mining algorithms may be used to "see" through this noise to discover useful patterns. The mining process may be directed toward, for example, elucidating new drug side effects and/or interactions among drugs and/or diseases.

Another medical application of the methods and systems is to facilitate personalizing healthcare. For instance, as the cost of gene sequencing drops, it is expected that people routinely will have their genes sequenced. This patient-specific genetic data may be correlated with an individual's health history and/or health-related behaviors to, for example, identify new diagnostic procedures and personalized therapies for medical conditions.

To encourage user participation, incentives may be provided and/or the data may be anonymized to address patient privacy concerns. For example, a third-party payor may require a subscriber to file a report as a condition of renewing a prescription for medication or to qualify for a lower co-payment/rate. In another embodiment, coupons for discounts on goods and/or services can be offered. With regard to anonymity, for example, no identifying information may be required (such as name and address) and instead an anonymous ID (e.g., passport ID) may be assigned to a user. An anonymous ID allows for separate health reports from the same individual to be linked together without associating identifying information with the data.

Another way to encourage participation is through minimizing the effort needed for a user to interact with the system. For instance, a free-text entry system with intelligent spelling correction can be provided for data entry. Text mining algorithms can be employed to extract structured data from the entered free-text. In another embodiment, a bar-code reader can be used to scan the label of a medication bottle. By way of another example, at the time of each report, the user can be asked health-related questions. The questions can be selected at random from a large library of questions or more particularly tailored to the user's condition/context. Data can be entered at will (e.g., symptoms such as chest pains, level of arthritis pain, etc.) and/or the user may request that reminders be sent (e.g., periodic email, etc). The individual data can be aggregated across a large group and patterns can be discovered from the data using, for example, algorithms that use low-order sufficient statistics and statistical methods that can make inferences with missing data (e.g., expectation-maximization (EM) algorithm).

The interface can be programmed to maximize the value of information while minimizing the effort required to provide the information. For example, questions may be selected automatically in a manner so as to converge on meaningful information and to otherwise maximize the value of the extracted information in conjunction with the already mined data. One way to accomplish this is to increase the number of patients being asked the same questions when the answers to randomized questions start showing a distinct but weak pattern in order to confirm the pattern. The patterns in free text may suggest an effect that needs further exploration with new questions, for instance, questions that were previously found to be informative when asked in conjunction with the observed pattern.

Another way to increase usage is to make many people aware of the service. By way of example, health-related keywords may be purchased on a search site (e.g., MSN SEARCH). When a user types a query containing one of the purchased keywords, the user is presented with a link to a web site enabling data collection. Other advertising venues may be employed (e.g., print, radio, TV, etc) and these ads may contain catchy phrase to describe the process of filing a report (e.g., encourage people to send in their "drug bugs").

The methods and systems can be utilized to generate revenue. For instance, the conclusions, discovered knowledge and/or the raw data may be forwarded to health-related agencies and/or private companies (e.g., pharmaceutical, biotechnology, medical device, etc.) or these entities may be otherwise given access to the data (e.g., an interface to access the database) for a fee. By way of example, the fee may be applied on a per use basis or a subscription service may be provided (i e., payment for unlimited or limited access to the database for a period of time).

One exemplary system that facilitates large-scale reporting of health-related data comprises a data collection component, a database and an aggregation component. The data collection component collects health-related data on a large-scale relating to a non-selected population. The database stores at least some of the health-related data. The aggregation component facilitates automatically ascertaining at least one pattern from the health-related data at least in part by applying one or more statistical, data-mining or machine-learning techniques to the database. The one or more techniques can comprise an expectation-maximization algorithm. The data collection component and the aggregation component can be encoded by computer-executable instructions stored on computer-readable media.

The health-related data can be any type of information relating to health, such a drug-related event, a symptom, a device output, an activity, or patient-specific genetic information. In addition to explicitly provided data, the data collection component can implicitly and/or automatically collect at least some of the health-related data. Moreover, the data collection component can accept data in a variety of forms, such as a free-text entry system, a bar-code reader, and/or a free-text entry system with intelligent spelling correction.

The data collection component can collect at least some of the health-related data by prompting a user with at least one question. In addition, the data collection component can determine one or more follow-up questions to present to the user based on the user's answer to the previous question. The data collection component can employ a Human Interactive Proof. The data collection component can anonymize the health-related data.

The system can further comprise a forwarding component to forward at least one pattern to a third party. The third party can be charged a fee to receive the pattern. The pattern can be forwarded to the third party via a data signal. The system can further comprise a reminder component, and, in one embodiment, the reminder component can automatically send one or more alerts to a user.

One exemplary method of extracting health observations from information obtained on a macro-scale comprises receiving information about a plurality of self-selected subjects, pooling the information, mining the pooled information at least in part by employing one or more statistical, data-mining or machine-learning algorithms to infer one or more health observations from the pooled information, and monetizing the one or more health observations. The method can further comprise providing at least some of the plurality of self-selected subjects with at least one incentive to self-select to supply information. The method can further comprise advertising the incentive and advertising the incentive can comprise obtaining the rights to one or more health-related keywords on a search site.

One exemplary online system to facilitate global medical data analysis comprises means for obtaining medical data from a global, unselected population via the Internet and means for automatically drawing conclusions from the medical data. The means for automatically drawing conclusions from the medical data can employ one or more statistical, data-mining, machine-learning or artificial intelligence algorithms to draw at least one conclusion from the medical data.

The following description and the annexed drawings set forth in detail certain illustrative aspects of the subject invention. These aspects are indicative, however, of but a few of the various ways in which the principles of the subject invention may be implemented. Other advantages and novel features of the invention will become apparent from the following detailed description of the invention when considered in conjunction with the drawings.

BRIEF DESCRIPTION OF THE DRAWINGS

FIG. 6 is an illustration of another example of an interface for reporting health-related information.

DETAILED DESCRIPTION

Figure 1:
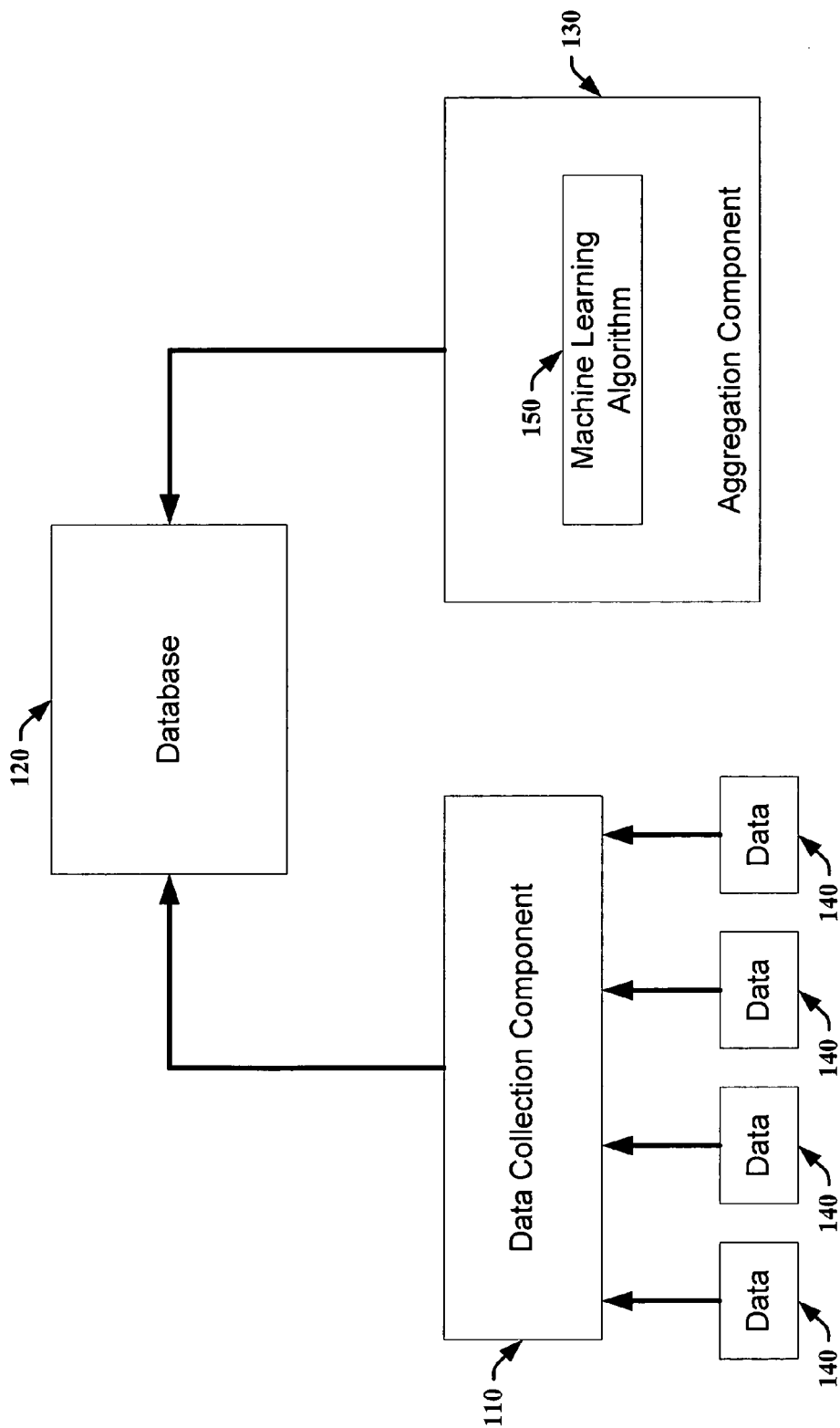
FIG. 1 is a block diagram of one example of a system that facilitates health-information reporting.

Various aspects of the subject invention are now described with reference to the drawings, wherein like reference numerals are used to refer to like elements throughout. In the following description, for purposes of explanation, numerous specific details are set forth in order to provide a thorough understanding of the subject invention. It may be evident, however, that the subject invention may be practiced without these specific details. In other instances, well-known structures and devices are shown in block diagram form in order to facilitate describing the subject invention. Although the methodologies are shown in the figures and described as a series of blocks, the subject invention is not limited by the order of the blocks, as some blocks may occur in different orders and/or concurrently with other blocks. Moreover, not all illustrated blocks may be required to implement the methodologies.

FIG. 1 schematically illustrates one example of a system 100 that facilitates large-scale reporting of health-related data. The term large-scale is used herein to mean large enough to produce the desired results (e.g., large enough to facilitate discerning one or more patterns from health information related to a non-selected population). The system 100 comprises a data collection component 110, a database 120 and an aggregation component 130. The data collection component 110 collects data 140 on a large-scale from a non-selected population and provides the data 140 to the database 120. The term non-selected is used herein to differentiate from studies on selected populations such as conventional clinical trials (which enroll subjects according to enrollment criteria) and public health studies (which focus on particular groups within the population). The aggregation component 130 applies a machine-learning algorithm 150 to the database 120 to discern patterns in the data 140. The data collection component 110 and aggregation component 130 can be the same process executing on a single or a plurality of computers or multiple processes executing on a single or a plurality of computers. Similarly, the database 120 can be a single datastore or multiple datastores. Moreover, the components 310, 330 and the database 320 can be implemented by software or combinations of software and hardware.

The data collection component 110 can collect any type of data 140 including but not limited to biological, pathophysiological, physiological, medical, healthcare and/or otherwise health-related. The data 140 can be, for example, a drug-related event, a symptom, and/or genetic information. The data collection component 110 can collect data 140 in any form including but not limited to textual, graphical, photographic, sound, speech, video, multimedia and the like. By way of example, the data collection component 110 can allow for free-text analysis. In this embodiment, rather than prompting a user with forms, a user enters the data in free-text form and the system automatically extracts and structures data from the free-text. The free-text analysis may include intelligent spelling correction or voice recognition. The user can be a consumer or a provider of healthcare services or any other source of health-related information. The data component 110 also can allow for input to be received in multiple forms in combination, such as both free-text and survey forms. The data 140 even can be introduced in the form of an activity, such as a memory game that a user plays to assess memory function.

The data collection component 110 can automatically obtain data 140, such as by querying a provider database (not shown). The data 140 can be provided to the data collection component 110 from any input means, such as a PDA, telephone, bar code reader, computer, keyboard, mouse, microphone, touchscreen, database, cell phone, etc. To promote participation through convenience of use, sites for data entry, such as kiosks with computer terminals, can be provided at public and other locations.

In one embodiment, the data collection component 110 can collect the data 140 anonymously such that no identifying information is linked to the data 140. By way of example, a user can be anonymously issued an ID, and use this ID to log on to the system 100 to enter data 140. The data from a particular individual can be linked together via this ID without associating the user's identity with the data. Alternatively, the data can be received by the data collection component 110 in conjunction with identifying information, and the data collection component 110 can filter the identifying information (privacy filter) prior to storage in the database 120. In addition, the data collection component 110 can employ various security measures to obtain data 140, such as a Human Interactive Proof (HIP) to verify that a human being (rather than an automated process) is providing the data 140.

The data 140 in whole or in part is sent to the database 120 to be stored for use by the aggregation component 130. The aggregation component 130 aggregates individual data across a large group and facilitates automatically detecting one or more patterns from the data 140 at least in part by utilizing machine-learning techniques 150 to mine the database 120. The term pattern as used herein includes but is not limited to trends, associations, correlations, connections, links, relationships, etc. By way of example, the aggregation component 130 can detect a correlation between the use of a certain medication and, for instance, a symptom across a large group of people. The aggregation component 130 can be structured to accord different weights to different data. For instance, data from a physician may be given a higher weight than data from a patient. By way of another example, data more likely to be accurate may be assigned a greater weight. Moreover, the aggregation component 130 can classify the data 140 according to demographics (e.g., age, gender, race, etc.) in order to facilitate recognizing demographic-specific patterns.

The patterns can be ascertained, for example, by employing an algorithm 150 that uses low-order sufficient statistics and statistical methods that can make inferences with missing data (e.g., expectation-maximization (EM) algorithm). Any machine-learning algorithm 150 can be employed, such as neural networks, expert systems, Bayesian belief networks, fuzzy-logic, data fusion engines and the like. The aggregation component 130 also can employ combinations of various artificial intelligence techniques to discern patterns. Moreover, a human intervention step may be combined with the machine-learning algorithm 150 to discern patterns from the data 140.

In one embodiment, the data collection component 110 and the aggregation component 130 can function together to collect and aggregate the data, such as by tailoring questions to converge on the most valued information. By way of example, the data collection component 110 can present a user with a question and the aggregation component 130 can apply machine-learning techniques 150 to the answer to determine a suitable follow-up question. A suitable follow-up question can be based on the user's response and/or patterns detected from the responses given by other users to the same or a similar question, for instance, to confirm a pattern. By way of example, a user may be presented with the question "How are you feeling today?" If the user's response is "I do not feel well today," the aggregation component 130 can choose the follow-up question "Please tell me about your symptoms." If the user responds "I have chest pain" and the system 100 has acquired data 140 from other users taking a particular type of medication that shows a pattern of chest pain associated with that particular medication, the system 100 can respond by asking the user "Please tell me what medications you are taking." By way of another example, a physician can be queried about the number of patients he/she has treated who are on a particular medication and who have experienced symptoms, such as chest pain. Moreover, questions can be tailored to the personal characteristics of the user, such as education level, language, culture and dialect.

In another embodiment, the system 100 can facilitate the design of personalized diagnostic and therapeutic regimens as well as alert/remind a user about behavior modifications that would benefit the user's health. By way of example, the data collection component 110 can obtain patient-specific genetic information as well as a variety of other relevant information from a user and/or provider and/or device, etc. The machine-learning component 150 can correlate the patient-specific genetic information with the other relevant information to draw conclusions about a user's health needs. For instance, if the patient-specific genetic information indicates that the person has a genetic susceptibility to heart disease and other relevant information indicates that the person smokes cigarettes and/or eats a high-fat diet and/or has a high cholesterol, the user can be sent an alert notifying him/her of various beneficial behavioral modifications that could reduce his/her risk of a heart attack (e.g., quitting smoking, reducing dietary fat, etc.) as well as advantageous medical therapies (e.g., cholesterol lowering drugs). By way of another example, if the patient-specific genetic information indicates the person is at high risk for a certain type of cancer, the person can be sent a reminder/alert to discuss with their physician various preventative therapies as well as useful diagnostic tests.

Figure 2:
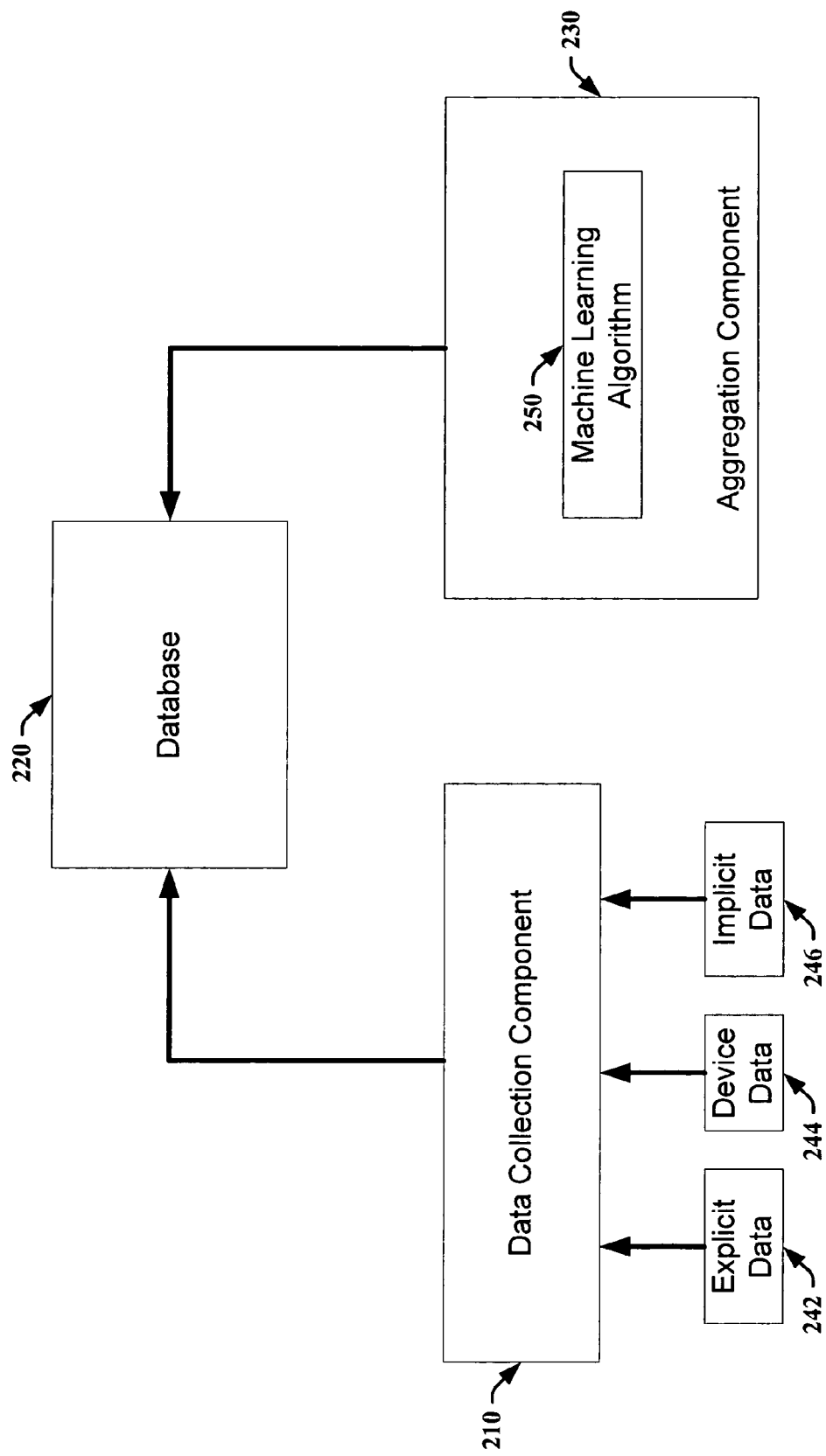
FIG. 2 is a block diagram of another example of a system that facilitates health-information reporting.

FIG. 2 schematically illustrates another example of a system 200 that facilitates large-scale reporting of health-related data. The system 200 comprises a data collection component 210, a database 220 and an aggregation component 230. The data collection component 210 can collect data 242-246 from a variety of different sources on a large-scale relating to a non-selected population and provides the data 240-260 in whole or in part to the database 220. The aggregation component 230 applies a machine-learning algorithm 250 to the database 220 to facilitate drawing conclusions from the data 242-246. The data collection component 210 and aggregation component 230 can be the same process executing on a single or a plurality of computers or multiple processes executing on a single or a plurality of computers. Similarly, the database 120 can be a single datastore or multiple datastores. Moreover, the components 210, 230 and the database 220 can be implemented by software or combinations of software and hardware.

As explained in relation to FIG. 1, a variety of different input means can be employed to provide the data 242-246. Data 242-246 can be received in a variety of different forms, such as explicit data 242 and/or implicit data 246. By way of example, explicit data 242 can be data directly entered by a patient or a provider (e.g., physician, nurse, pharmacy, hospital, institution, agency, device data 244, etc.).

In order to encourage participation, the data collection component 210 can automate the data collection process in whole or in part. For instance, the data collection component 210 can acquire implicit data 246. Implicit data 246 as used herein means data that is a by-product of the activities that people engage in and/or information that is provided to the system 200. By way of example, implicit data 246 may be acquired from explicit data 242. For instance, a user can be asked a broad question by the system 200, such as "How are you feeling?" The user can enter his/her answer in free-text form and the system 200 can interpret this answer to extract implicit data 246. If the user's answer is "I am not feeling well and my eyes are red and itchy and I am sneezing quite a bit," the system 200 can determine that the user has allergies. By way of another example, the data collection component 210 can automatically acquire a user's prescription medication history by querying a pharmacy database (not shown). By analyzing the user's refill history, the system 200 can determine whether the user is taking the medication as prescribed. The system 200 can employ various techniques and methodologies to gather the implicit data 246, such as a machine-learning algorithm 250.

The data collection component 210 also can receive device data 244. The data collection component 210 can interrogate devices to obtain the device data 244 and/or the devices can initiate data transfers. Any form of communication between the system 200 and the devices may be employed, such as direct connection, wireless connection, network connection, etc. By way of example, device data 244 can be data received from a smart scale that can automatically connect with the system 200 to send a patient's weight. Other devices that can send device data 244 include pacemakers, defibrillators, thermometers, consumer healthcare devices, electronic calendars, PDAs, cell phones, exercise equipment, and the like. For instance, a user can keep track of how often they have a particular symptom by entering this information into his/her electronic calendar. This information can be uploaded to the data collection component 210 by the electronic calendar, for instance, upon receiving a reminder, by user indication, and/or automatically without receiving a prompt. Alternatively, the system 200 can interrogate the electronic calendar. By way of another example, the devices can connect with the system 200 by using a platform such as MICROSOFT .NET.

Figure 3:
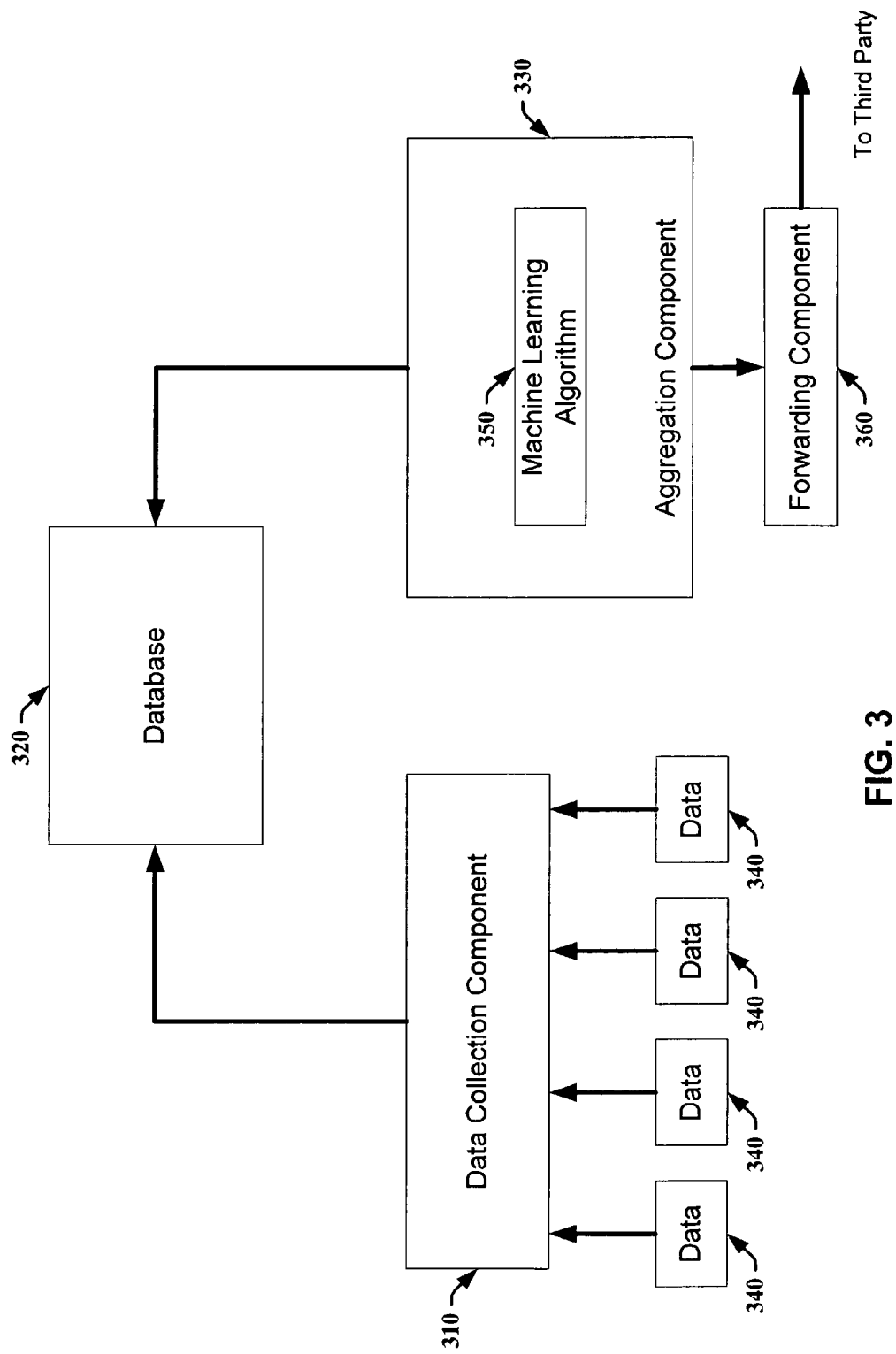
FIG. 3 is a block diagram of another example of a system that facilitates health-information reporting.

FIG. 3 schematically illustrates another example of a system 300 that facilitates large-scale reporting of health-related data. The system 300 comprises a data collection component 310, a database 320, an aggregation component 330 and a forwarding component 360. The data collection component 310 collects data 340 on a large-scale relating to a non-selected population and provides the data 340 in whole or in part to the database 320. The aggregation component 330 applies a machine-learning algorithm 350 to the database 320 to discern patterns in the data 340. The forwarding component 360 forwards at least one pattern to a third party. The forwarding component 360 can forward information in any form, including but not limited to a data signal, online transmission, wirelessly, email, telephone, facsimile, blackberry, cell phone, etc.

The components 310, 330 and 360 can be the same process executing on a single or a plurality of computers or multiple processes executing on a single or a plurality of computers. Similarly, the database 320 can be a single datastore or multiple datastores. Moreover, the components 310, 330 and 360 and the database 320 can be implemented by software or combinations of software and hardware.

The third party that receives the patterns from the system 300 can be a patient, a provider (e.g., physicians, hospitals, pharmacies, nursing homes, etc.), a governmental entity (e.g., Food & Drug Administration (FDA), lawmakers, etc.), a private entity (e.g., pharmaceutical companies, medical device companies, distributors, drug safety watchdog groups, insurance companies, AARP, etc.) and any other interested parties. By way of example, by mining the database 320 for associations between adverse events and medications, the system 300 can facilitate the early detection of drug side effects and/or drug interactions. The system 300 can forward this information to alert interested parties, such as the company that manufactures the medication(s) associated with the adverse event and/or the FDA. By way of another example, a user may register with the system 300 and sign-up for alerts relating to a medication the user is taking. If a pattern associated with the user's medication is recognized by the system 300, the forwarding component 360 can send an alert to the user notifying the user of the relationship.

The system 300 also can facilitate the detection of counterfeit drugs. By way of example, the data collection component 310 can collect information relating to a user's medication and-physiological status and correlate this information to determine if the medication is producing the intended effect. In one embodiment, the user can be queried about medications and the specific effects of those medications. Alternatively, a device can provide an output corresponding to a measure of the patient's response to the therapy. For instance, if a patient is taking blood pressure medication, the patient can enter the medication's name as well as the patient's blood pressure measurements via the data collection component 310. The system 300 can store this information over time and determine if the patient is adequately responding to the therapy, for instance, by employing machine-learning techniques 350. If the system 300 determines that the patient's response to the medication is inadequate, the forwarding component 360 may send the patient an alert.

The system 300 can forward the patterns to the interested parties in return for a fee. The fee can be structured in any manner, for instance, a fee can be charged for each alert sent to the third party. Alternatively, a subscription service can be provided such that a third party is charged a fee for unlimited or limited access to information inferred by the system 300 for a period of time.

Figure 4:
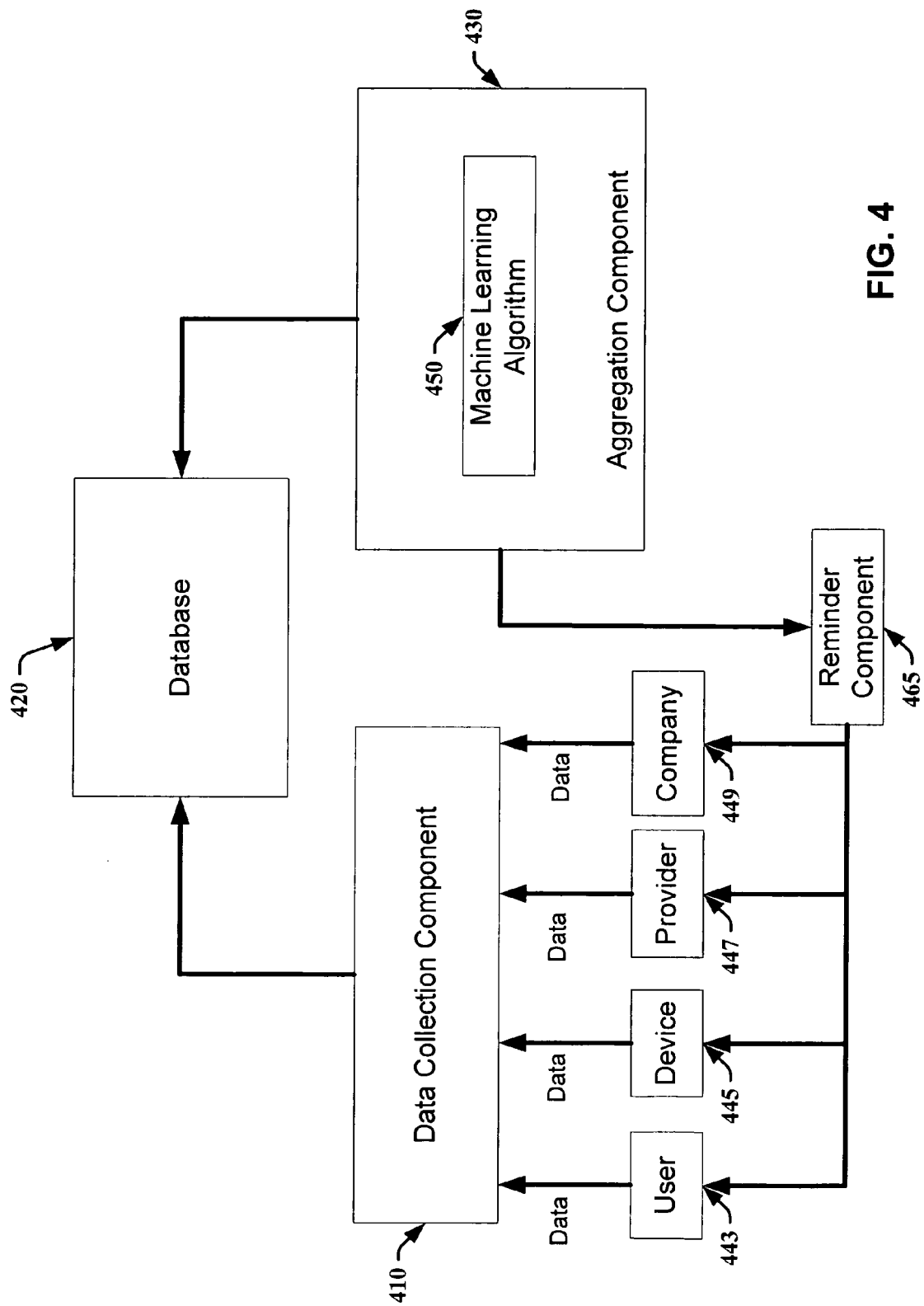
FIG. 4 is a block diagram of yet another example of a system that facilitates health-information reporting.

FIG. 4 schematically illustrates another example of a system 400 that facilitates large-scale reporting of health-related data. The system 400 comprises a data collection component 410, a database 420, an aggregation component 430 and a reminder component 365. The data collection component 410 collects data 440 on a large-scale from a non-selected population and provides the data 440 in whole or in part to the database 420. The aggregation component 430 applies a machine-learning algorithm 450 to the database 420 to discern patterns in the data 440. The reminder component 465 sends reminders to various entities 443-449. The reminder component 465 can send reminders in any form, including but not limited to a data signal, online transmission, wirelessly, email, telephone, facsimile, blackberry, cell phone, etc.

The components 410, 430 and 465 can be the same process executing on a single or a plurality of computers or multiple processes executing on a single or a plurality of computers. Similarly, the database 420 can be a single datastore or multiple datastores. Moreover, the components 410, 430 and 465 and the database 420 can be implemented by software or combinations of software and hardware.

The reminder component 465 can send reminders to remind various entities 443-449 to enter data. The reminders can be sent to any party/entity that requests to be reminded, such as users 443 (e.g., individuals, etc.), devices 445 (e.g., electronic calendars, consumer healthcare devices, pacemakers, etc.), providers 447 (e.g., physicians, nurses, hospitals, insurance companies, pharmacies, etc.) and companies 449 (e.g., pharmaceutical manufacturers, medical device manufacturers, distributors, etc.). Alternatively, the reminder component 465 can send out reminders automatically without receiving a request. For instance, the machine-learning component 450 can determine that information is missing from a profile and signal the reminder component 465 to send a request to the information source. Optionally, a fee can be charged for the reminder service. The reminder component 465 also can send alerts of the type described in relation to FIG. 3.

Figure 5:
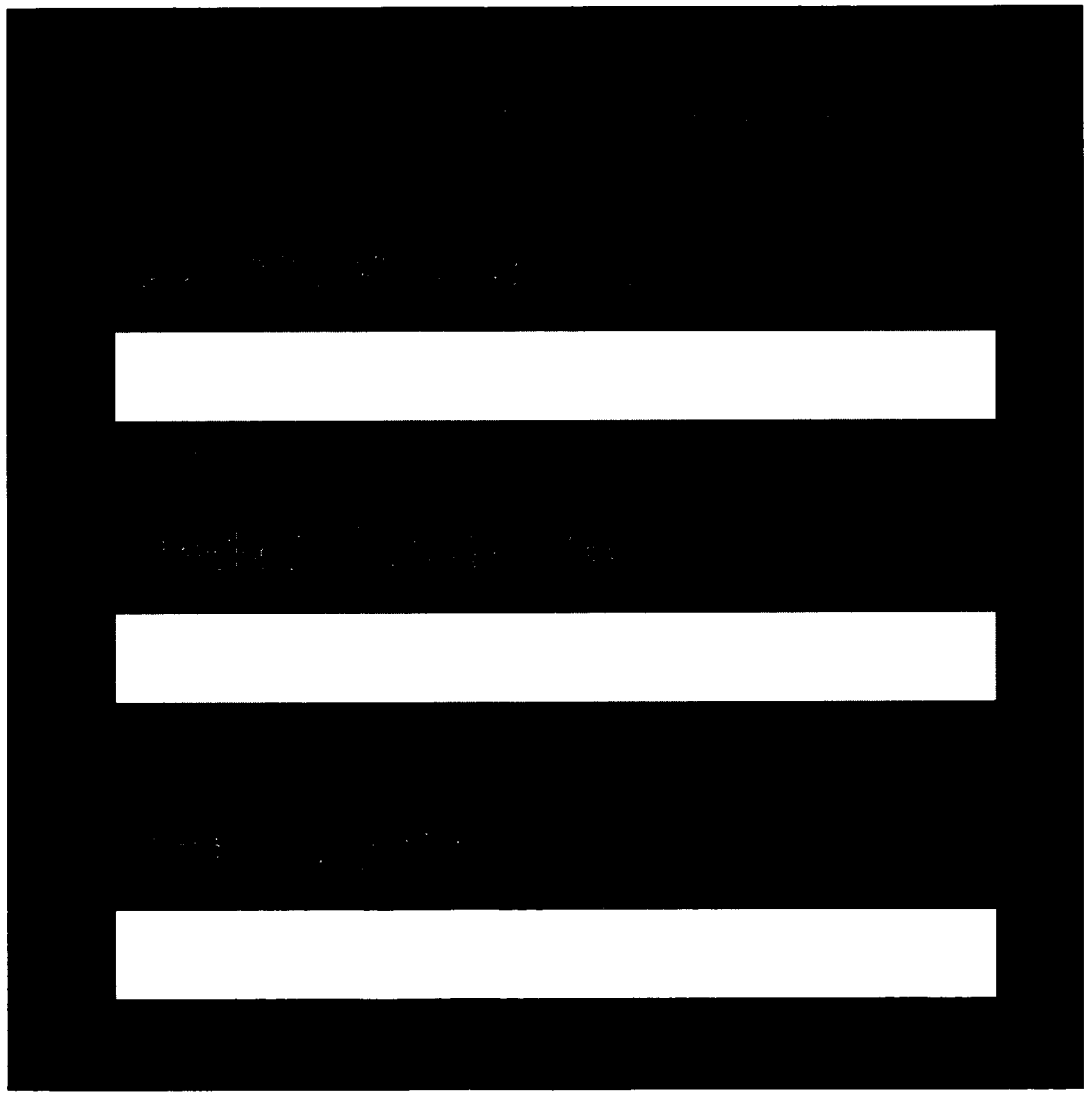
FIG. 5 is an illustration of one example of an interface for reporting health-related information.
Figure 6:
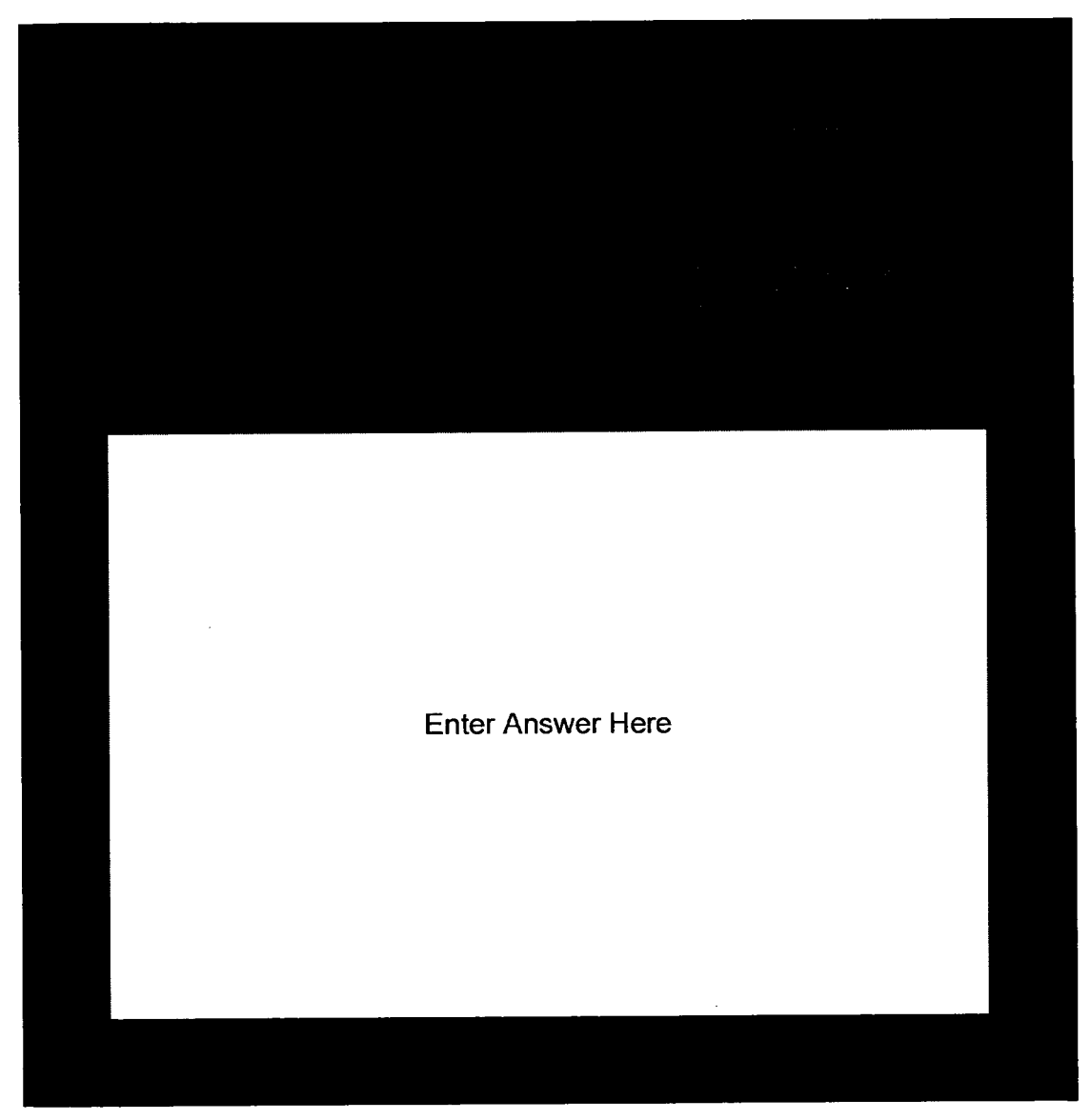

FIGS. 5 and 6 are illustrations of two examples of an interface for reporting health-related information. FIG. 5 illustrates a survey form 500 provided to a user by a data collection component to obtain information about the user. FIG. 6 illustrates a free-text form 600 provided to a user by a data collection component to obtain information about the user. A user can enter the information in any format and the data collection component will extract structured information by employing, for instance, an artificial intelligence process.

The systems described above can be implemented on a network, in whole or in part, by data signals. These manufactured data signals can be of any type and can be conveyed on any type of network. For instance, the systems can be implemented by electronic signals propagating on electronic networks, such as the Internet. Wireless communications techniques and infrastructures also can be utilized to implement the systems.

Figure 7:
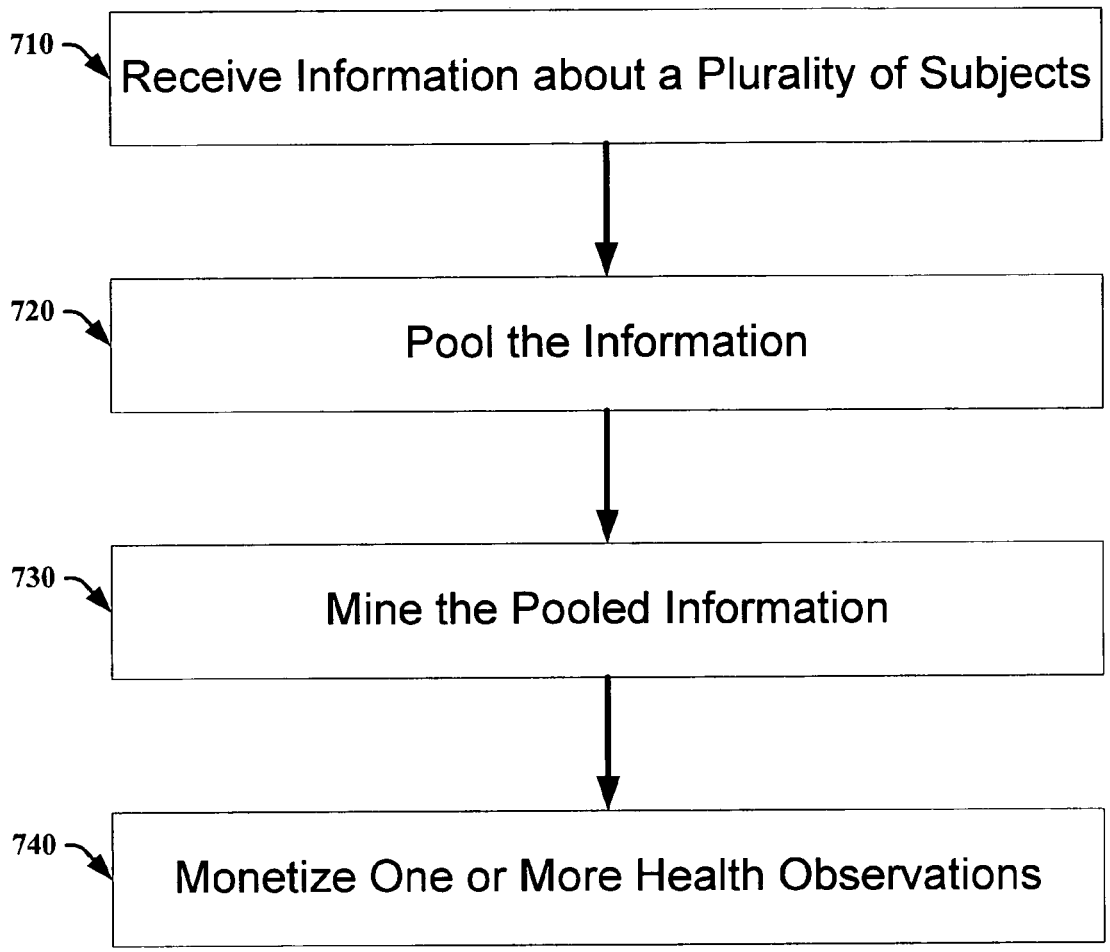
FIG. 7 is a flowchart representing one example of a method of extracting health observations.

FIG. 7 is a flowchart representing one example of a method 700 of extracting health observations from information obtained on a macro-scale. The method 700 can be implemented by computer-executable instructions stored on computer-readable media or conveyed by a data signal of any type. The method 700 can be implemented at least in part manually. The term macro-scale as used herein means on a scale sufficient to allow a machine-learning component to make reasonably valid inferences from pooled data.

At step 710, information about a plurality of self-selected subjects is received. The information can be obtained from a consumer or a provider of healthcare services or any other source of information, such as a device or an electronic calendar. At step 720, the information is pooled. At step 730, the pooled data is mined. The pooled information can be mined at least in part by employing a data-mining algorithm to infer one or more health observations from the pooled information. The term health observation as used herein includes but is not limited to trends, associations, correlations, connections, links, relationships, etc. At step 740, the one or more health observations are monetized. Monetizing the health observations can be accomplished, for instance, by charging an interested party a fee for access to the health observations. The fee can be structured in any manner, for instance, a fee can be charged for each alert sent to a third party. Alternatively, a subscription service can be provided such that a third party is charged a fee for unlimited or limited access to health observations over a period of time. The method 700 can be repeated an unlimited number of times as needed to generate health observations.

Any type of information can be pooled including but not limited to biological, pathophysiological, physiological, medical, healthcare and/or otherwise health-related. The information can be, for example, a drug-related event, a symptom, and/or genetic information. The data can be collected in any form including but not limited to textual, graphical, photographic, sound, speech, video, multimedia and the like. By way of example, the data can be collected by employing a free-text analysis, which optionally can include intelligent spelling correction or voice recognition. The data can be explicitly, implicitly and/or automatically input. The information can be entered by any input means, such as a PDA, telephone, bar code reader, computer, keyboard, mouse, microphone, touchscreen, database, cell phone, etc. Sources of information can be sent reminders either by request and/or inferred reminders.

In one embodiment, the information can be collected anonymously such that no identifying information is linked to the information. Alternatively, the data can be received in conjunction with identifying information and stripped of the identifying information by a privacy filter. Security measures can be employed in the information collection process, such as a Human Interactive Proof (HIP) to verify that a human being (rather than an automated process) is providing the data.

Any data-mining algorithm can be employed to mine the pooled data, such as an algorithm that uses low-order sufficient statistics and statistical methods that can make inferences with missing data (e.g., expectation-maximization (EM) algorithm). Other example of data-mining methods include but are not limited to neural networks, expert systems, Bayesian belief networks, fuzzy logic, data fusion engines and the like as well as combinations of various artificial intelligence techniques capable of discerning patterns. Moreover, a human intervention step may be combined with the data-mining algorithm to discern patterns.

In mining the pooled data, information can be accorded different weights, for instance, information from a pharmacy may be given a higher weight than information from a patient. By way of another example, information more likely to be accurate may be assigned a greater weigh. By way of yet another example, the machine-learning algorithm can classify the information according to demographics (e.g., age, gender, race, etc.) in order to facilitate making demographic-specific health observations.

Figure 8:
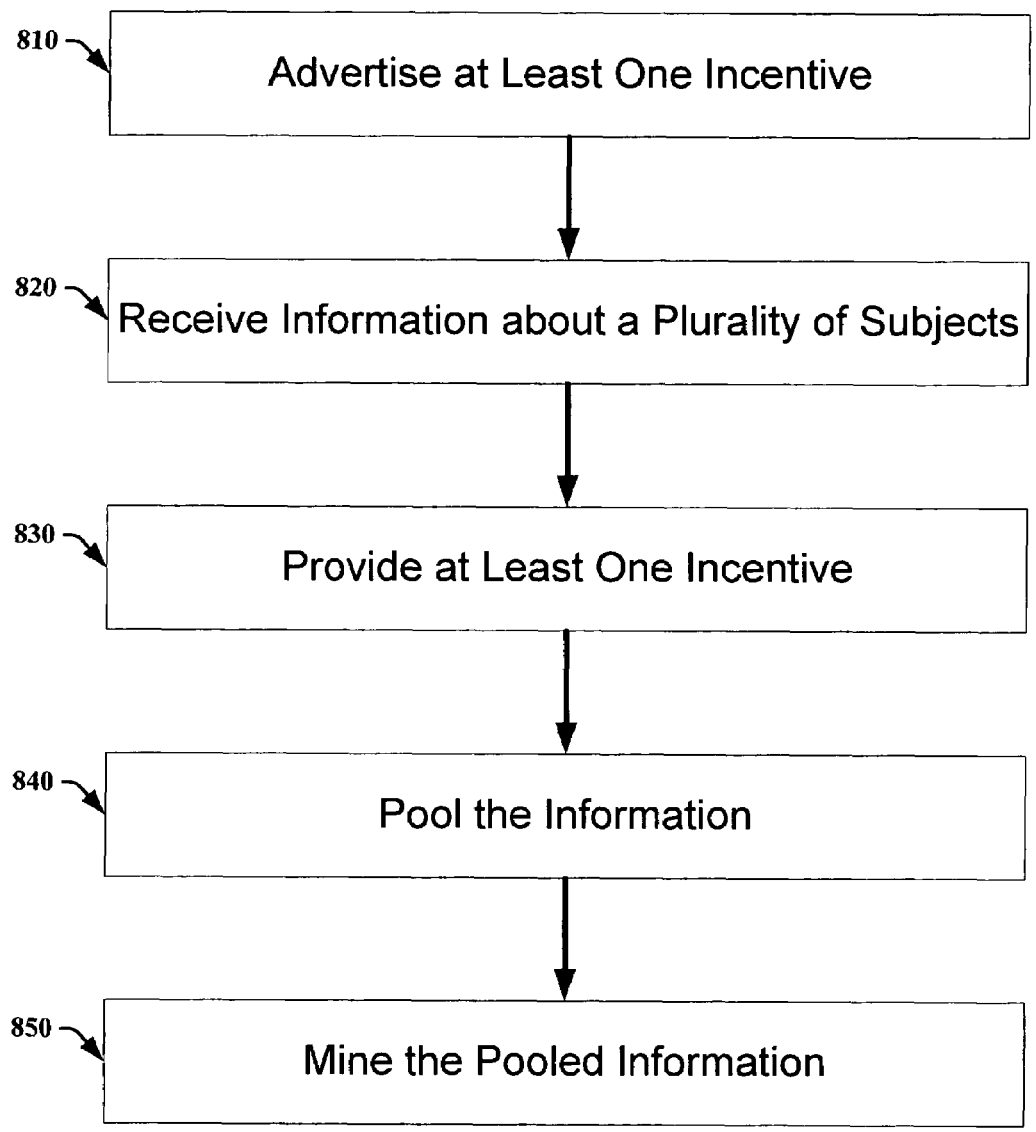
FIG. 8 is a flowchart representing another example of a method of extracting health observations.

FIG. 8 is a flowchart representing another example of a method 800 of extracting health observations from information obtained on a macro-scale. The method 800 can be implemented by computer-executable instructions stored on computer-readable media or conveyed by a data signal of any type. The method 800 can be implemented at least in part manually.

At step 810, at least one incentive to supply information is advertised. The incentive can be advertised, for example, on a search site upon entering a search string containing one or more keywords. Any other means of advertising can be used to advertise the incentive, such as print, TV, radio, online ad, etc. At step 820, information about a plurality of self-selected subjects is received. At step 830, the incentive is provided to the self-selected subject. The incentive can be of any type and can be a requirement or a bonus. For instance, an insurance company (e.g., Medicare, Medicaid, private insurer, etc.) may require a subscriber to file a report as a condition of renewing a prescription for medication or to qualify for a lower co-payment/rate. By way of another example, coupons for discounts on goods and services can be offered. At step 840, the information is pooled. At step 850, the pooled data is mined. The pooled information can be mined at least in part by employing a data-mining algorithm to infer one or more health observations from the pooled information. The method 800 can be repeated an unlimited number of times as needed to generate health observations. Moreover, the method 800 is not limited to the order shown in the flowchart. For instance, step 830 can be performed prior to step 820.

As described in relation to FIG. 7 above, the information can be entered anonymously or stripped of identifying information. The information can be obtained from a consumer or a provider of healthcare services or any other source of information, such as a device or an electronic calendar, can be in any form and can be provided by any input means. The data-mining algorithm also can be of any type.

Figure 9:
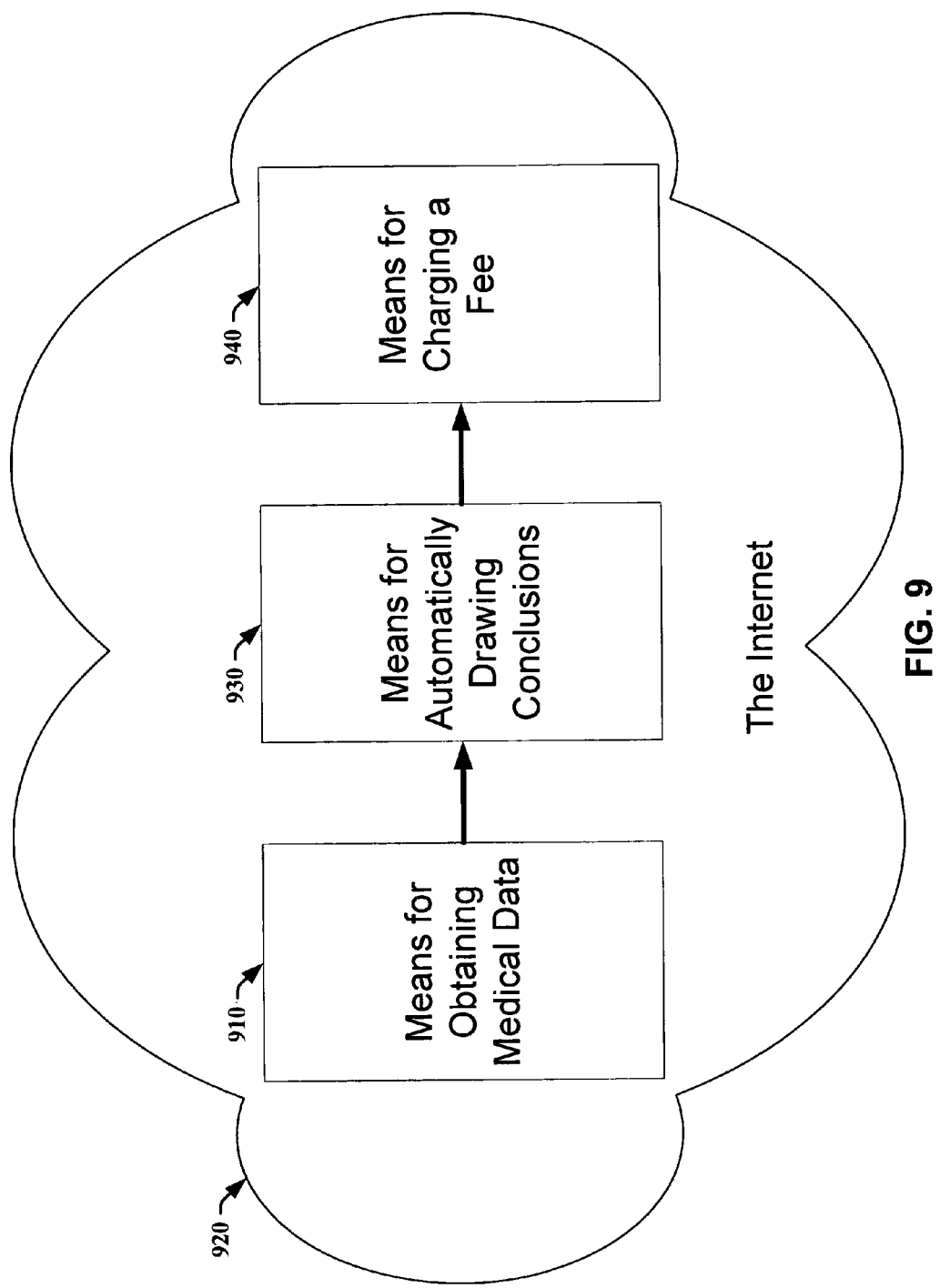
FIG. 9 is a block diagram of one example of a system to facilitate large-scale medical data analysis.

FIG. 9 is a block diagram of one example of an online system 900 to facilitate global medical data analysis. The term global as applied to the online system 900 and used herein means an online system capable of reaching a geographically, wide-spread population. The system 900 includes means for obtaining medical data from a global, unselected population 910 via the Internet 920 and means for automatically drawing conclusions from the medical data 930. The means for automatically drawing conclusions from the medical data 930 can employ one or more artificial intelligence algorithms to draw at least one conclusion from the medical data. Optionally, the system 900 can include a means for charging a fee 940. In one embodiment, the fee can be charged to receive the conclusions drawn by the artificial intelligence algorithms. In another embodiment, the fee can be assessed to gain access to the system 900.

The structures and algorithms described in relations to FIGS. 1-8 above can be used to implement the means 910, 930 and 940 of the system 900. As described in relation to FIGS. 1-8, the data can be entered anonymously or stripped of identifying information. The information can be obtained from a consumer or a provider of healthcare services or any other source of information, such as a device or an electronic calendar, can be in any form and can be provided by any input means. The data-mining algorithm also can be of any type.

As used in this application, the term "means" is intended to refer to a computer-related entity, either hardware, a combination of hardware and software, software, or software in execution. For example, a means may be, but is not limited to being, a process running on a processor, a processor, an object, an executable, a thread of execution, a program, and/or a computer. By way of illustration, both an application running on a server and the server can be a means. One or more means may reside within a process and/or thread of execution and a means may be localized on one computer and/or distributed between two or more computers. A "thread" is the entity within a process that the operating system kernel schedules for execution. As is well known in the art, each thread has an associated "context" which is the volatile data associated with the execution of the thread. A thread's context includes the contents of system registers and the virtual address belonging to the thread's process. Thus, the actual data comprising a thread's context varies as it executes.

The subject invention may operate in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired in various instances of the subject invention.

As used in this application, the term "component" is intended to refer to a computer-related entity, either hardware, a combination of hardware and software, software, or software in execution. For example, a component may be, but is not limited to, a process running on a processor, a processor, an object, an executable, a thread of execution, a program, and a computer. By way of illustration, an application running on a server and/or the server can be a component. In addition, a component may include one or more subcomponents. One or more components may reside within a process and/or thread of execution and a component may be localized on one computer and/or distributed between two or more computers.

Figure 10:
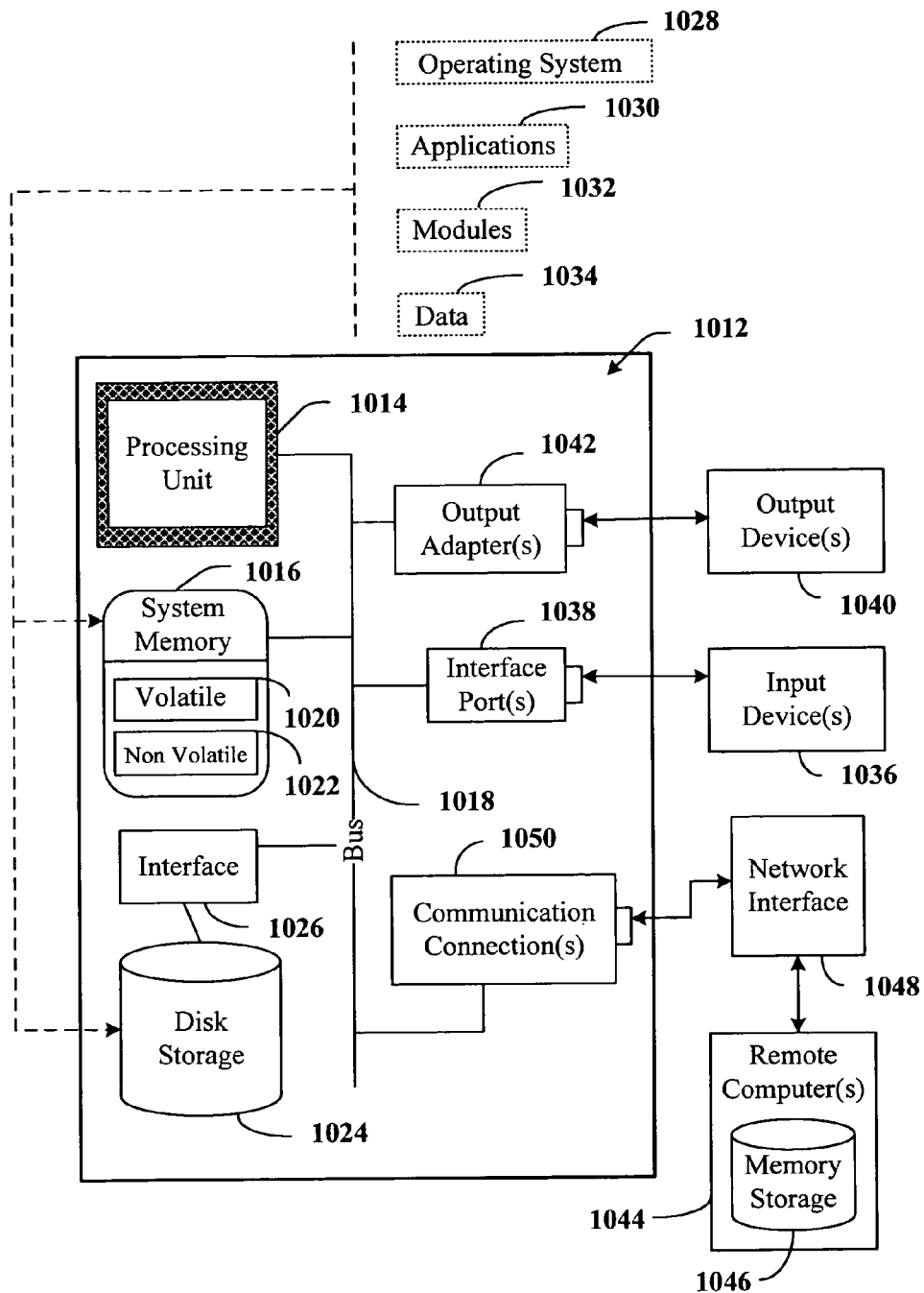
FIG. 10 illustrates an exemplary computing architecture.
Figure 11:
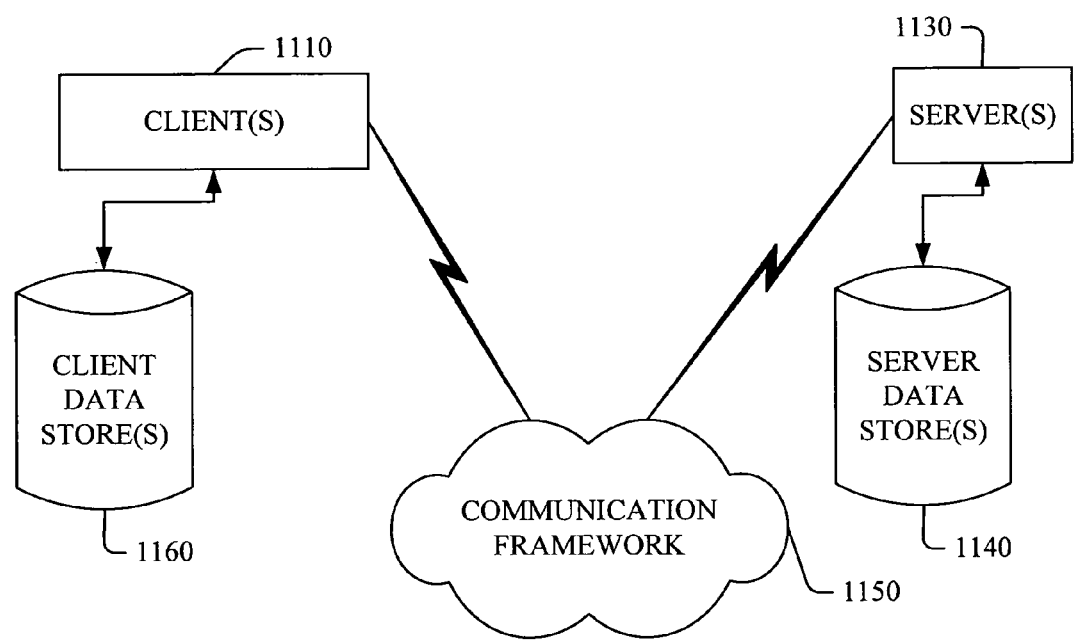
FIG. 11 illustrates an exemplary networking environment.

In order to provide a context for the various aspects of the invention, FIGS. 10 and 11 as well as the following discussion are intended to provide a brief, general description of a suitable computing environment in which the various aspects of the user interfaces, methods and systems described herein may be implemented. Although the description above relates to the general context of computer-executable instructions of a computer program that runs on a computer and/or computers, those skilled in the art will recognize that the user interface, methods and systems also may be implemented in combination with other program modules. Generally, program modules include routines, programs, components, data structures, etc. that perform particular tasks and/or implement particular abstract data types.

Moreover, those skilled in the art will appreciate that the user interfaces, methods and systems described herein may be practiced with other computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules may be located in both local and remote memory storage devices. The user interface, methods and systems described herein may be embodied on a computer-readable medium having computer-executable instructions for implementing various aspects of the subject invention as well as signals manufactured to transmit such information, for instance, on a network.

FIG. 10 schematically illustrates an exemplary environment 1010 for implementing various aspects of the subject invention. The environment 1010 includes a computer 1012, which includes a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014.

The system bus 1018 can be any of several types of bus structure(s) including the memory bus or memory controller, a peripheral bus or external bus, and/or a local bus using any variety of available bus architectures including, but not limited to, 10-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCM-CIA), and Small Computer Systems Interface (SCSI).

The system memory 1016 includes volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), or flash memory. Volatile memory 1020 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and Rambus Direct RAM (RDRAM), direct Rambus dynamic RAM (DRDRAM), and Rambus dynamic RAM (RDRAM).

Computer 1012 also includes removable/non-removable, volatile/non-volatile computer storage media. FIG. 10 illustrates, for example a disk storage device 1024. Disk storage device 1024 includes, but is not limited to, devices like a magnetic disk drive, floppy disk drive, tape drive, Jaz drive, Zip drive, LS-100 drive, flash memory card, or memory stick. In addition, disk storage device 1024 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1024 to the system bus 1018, a removable or non-removable interface is typically used such as interface 1026.

In addition to hardware components, FIG. 10 illustrates software that acts as an intermediary between users and the basic computer resources described in suitable operating environment 1010. Such software includes an operating system 1028. Operating system 1028, which can be stored on disk storage devices 1024, acts to control and allocate resources of the computer system 1012. System applications 1030 take advantage of the management of resources by operating system 1028 through program modules 1032 and program data 1034 stored either in system memory 1016 or on disk storage devices 1024. The subject invention can be implemented with various operating systems or combinations of operating systems.

A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port may be used to provide input to computer 1012 and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a personal computer, a server, a router, a network PC, a workstation, a microprocessor based appliance, a peer device or other common network node and the like, and typically includes many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1050 refers to the hardware/software employed to connect the network interface 1048 to the bus 1018. While communication connection 1050 is shown for illustrative clarity inside computer 1012, it can also be external to computer 1012. The hardware/software necessary for connection to the network interface 1048 includes, for exemplary purposes only, internal and external technologies such as, modems including regular telephone grade modems, cable modems and DSL modems, ISDN adapters, and Ethernet cards.

FIG. 11 is a schematic block diagram of a sample-computing environment 1100 with which the present invention can interact. The system 1100 includes one or more client(s) 1110. The client(s) 1110 can be hardware and/or software (e.g., threads, processes, computing devices). The system 1100 also includes one or more server(s) 1130. The server(s) 1130 can also be hardware and/or software (e.g., threads, processes, computing devices). The servers 1130 can house threads to perform transformations by employing the user interfaces, methods and systems described herein. One possible communication between a client 1110 and a server 1130 can be in the form of a data packet adapted to be transmitted between two or more computer processes. The system 1100 includes a communication framework 1150 that can be employed to facilitate communications between the client(s)

1110 and the server(s) 1130. The client(s) 1110 can connect to one or more client data store(s) 1160 that can be employed to store information local to the client(s) 1110. Similarly, the server(s) 1130 can connect to one or more server data store(s) 1140 that can be employed to store information local to the servers 1130.

What has been described above are examples of the subject invention. It is, of course, not possible to describe every conceivable combination of components or methodologies, but one of ordinary skill in the art will recognize that many further combinations and permutations of the subject invention are possible. Accordingly, the subject invention is intended to embrace all such alterations, modifications and variations that fall within the spirit and scope of the claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates large-scale reporting of health-related data, comprising:
   a data collection component to collect health-related data on a large-scale relating to a non-selected population wherein at least some of the health-related data is collected by prompting a user with a first question;
   a database to store at least some of the health-related data; and
   an aggregation component to facilitate automatically ascertaining at least one pattern from the health-related data, the aggregation component automatically ascertaining the at least one pattern from the health-related data at least in part by applying one or more of a statistical technique, a data mining technique or a machine-learning technique to the database, the aggregation component with the data collection component ascertains the at least one pattern by further determining a follow-up question based on of the user's answer to the first question and at least one pattern detected from responses given by other users to the first question.

2. The system of claim 1, wherein the health-related data is at least one of a drug-related event, a symptom, a device output, an activity, and patient-specific genetic information.

3. The system of claim 1, wherein the data collection component implicitly collects at least some of the health-related data.

4. The system of claim 1, wherein the data collection component automatically collects at least some of the health-related data.

5. The system of claim 1, wherein the one or more machine-learning techniques comprise an expectation-maximization algorithm.

6. The system of claim 1, wherein the data collection component comprises at least one of a free-text entry system, a bar-code reader, and a free-text entry system with intelligent spelling correction.

7. The system of claim 1, further comprising a forwarding component to forward the at least one pattern to a third party.

8. The system of claim 7, wherein the third party is charged a fee to receive the at least one pattern.

9. The system of claim 7, wherein the at least one pattern is forwarded to the third party via a data signal.

10. The system of claim 1, further comprising a reminder component to automatically send one or more alerts to a user.

11. The system of claim 1, wherein the data collection component employs a Human Interactive Proof.

12. The system of claim 1, wherein the data collection component anonymizes the health-related data.

13. The system of claim 1, wherein the data collection component and the aggregation component are encoded by computer-executable instructions stored on computer-readable media.

14. A method of extracting health observations from information obtained on a macro-scale, comprising:
   receiving information about a plurality of self selected subjects, at least some of the information is obtained by prompting at least one of the subjects with a first question;
   confirming pattern in user responses by determining a follow-up question based on the subject's response to the first question and at least one pattern detected from responses given by other subjects to the first question;
   pooling the information;
   mining the pooled information at least in part by employing one or more of a statistical algorithm, a data-mining algorithm and a machine-learning algorithm to infer one or more health observations from the pooled information; and
   monetizing the one or more health observations.

15. The method of claim 14, further comprising providing at least some of the plurality of self-selected subjects with at least one incentive to self-select to supply information.

16. The method of claim 15, further comprising advertising the at least one incentive.

17. The method of claim 16, wherein advertising the at least one incentive comprises obtaining the rights to one or more health-related keywords on a search site.

18. An online system to facilitate global medical data analysis, comprising:
   means for obtaining medical data from a global, unselected population via the Internet wherein at least some of the data is obtained by prompting at least one user with an initial query; and
   means for automatically drawing conclusions from the medical data, the means for automatically drawing conclusions from the medical data employing one or more of a statistical algorithm, a machine-learning algorithm, a data-mining algorithm and an artificial-intelligence algorithm to draw at least one conclusion from the medical data, the means for automatically drawing conclusions functions with the means for obtaining medical data to confirm at least a pattern in user's responses by further determining a follow-up query based on the user's response to the initial query and at least one pattern detected from responses given by other users to the initial query.

19. The system of claim 1, the aggregation component ascertains the at least one pattern by increasing number of users being asked same questions when answers to randomized questions start showing a distinct pattern.

20. The system of claim 1, the aggregation component is structured to accord different weights to different data based at least on a likely accuracy of the different data.

* * * * *

UNITED STATES PATENT AND TRADEMARK OFFICE
CERTIFICATE OF CORRECTION

| | | |
|---|---|---|
| PATENT NO. | : 7,406,453 B2 | Page 1 of 1 |
| APPLICATION NO. | : 11/266974 | |
| DATED | : July 29, 2008 | |
| INVENTOR(S) | : Craig J. Mundie et al. | |

It is certified that error appears in the above-identified patent and that said Letters Patent is hereby corrected as shown below:

In Drawings, in Sheet 1 of 11, FIG. 1, line 1, above "Reference numeral 110" insert -- 100 --.

In Drawings, in Sheet 2 of 11, FIG. 2, line 1, above "Reference numeral 210" insert -- 200 --.

In Drawings, in Sheet 3 of 11, FIG. 3, line 1, above "Reference numeral 310" insert -- 300 --.

In Drawings, in Sheet 4 of 11, FIG. 4, line 1, above 'Reference numeral 410" insert -- 400 --.

In Drawings, in Sheet 5 of 11, FIG. 5, line 1, above "FIG. 5" insert -- 500 --.

In Drawings, in Sheet 6 of 11, FIG. 6, line 1, above "FIG. 6" insert -- 600 --.

In Drawings, in Sheet 7 of 11, FIG. 7, line 1, above "Reference numeral 710" insert -- 700 --.

In Drawings, in Sheet 8 of 11, FIG. 8, line 1, above "Reference numeral 810" insert -- 800 --.

In Drawings, in Sheet 9 of 11, FIG. 9, line 1, above "Reference numeral 920" insert -- 900 --.

In Drawings, in Sheet 10 of 11, FIG. 10, line 1, above "Reference numeral 1028" insert -- 1010 --.

In Drawings, in Sheet 11 of 11, FIG. 11, line 1, above "Reference numeral 1110" insert -- 1100 --.

In column 15, line 38, in Claim 1, after "on" delete "of".

In column 16, line 13, in Claim 14, delete "self selected" and insert -- self-selected --, therefor.

Signed and Sealed this
Third Day of May, 2011

David J. Kappos
*Director of the United States Patent and Trademark Office*